United States Patent
van den Bosch et al.

(10) Patent No.: US 9,313,961 B2
(45) Date of Patent: Apr. 19, 2016

(54) WHITE-STEM TRAIT CONTAINING PLANTS

(75) Inventors: Frans van den Bosch, Kesteren (NL); Meindert Boon, Scharwoude (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 855 days.

(21) Appl. No.: 13/090,603

(22) Filed: Apr. 20, 2011

(65) Prior Publication Data

US 2011/0265201 A1    Oct. 27, 2011

Related U.S. Application Data

(60) Provisional application No. 61/326,036, filed on Apr. 20, 2010.

(51) Int. Cl.
*A01H 5/04* (2006.01)
*A01H 5/10* (2006.01)

(52) U.S. Cl.
CPC ... *A01H 5/04* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 5,710,364 A * | 1/1998 | Shintaku | 800/306 |
| 7,759,550 B2 | 7/2010 | Mozsar et al. | |
| 8,084,669 B2 | 12/2011 | Boon et al. | |
| 2004/0117877 A1 * | 6/2004 | Van den Bosch et al. | 800/306 |
| 2006/0277637 A1 | 12/2006 | Mozsar et al. | |
| 2008/0127362 A1 * | 5/2008 | Boon et al. | 800/266 |
| 2013/0007906 A1 * | 1/2013 | van den Bosch et al. | 800/260 |

FOREIGN PATENT DOCUMENTS

| | | |
|---|---|---|
| CN | 1180744 A | 5/1998 |
| CN | 101610668 A | 12/2009 |
| EP | 0662281 A2 | 7/1995 |
| WO | WO 2007/062009 A2 | 5/2007 |
| WO | WO 2008/042392 A2 | 4/2008 |
| WO | WO 2010/023093 A1 | 3/2010 |
| WO | WO 2010023093 A1 * | 3/2010 |

OTHER PUBLICATIONS

Pudeslki et al. (209) PNAS 106: 12201-12206.*
Robertson and Earle (1986) Plant Cell Rep. 5: 61-64.*
David and Tempe (1988) Plant Cell Rep. 7: 88-91.*
Raven et al., Biology of Plants, sixth edition, 1999, W.H. Freeman and Co. Worth Publishers, New York, NY, pp. 912-913.*
Supplemental European Search Report issued Sep. 16, 2013, in European Application No. 11772641.4.
English translation of search report issued with office action on Aug. 22, 2013, in Chinese Application No. 201180023982.0.

\* cited by examiner

*Primary Examiner* — Elizabeth McElwain
(74) *Attorney, Agent, or Firm* — Dentons US LLP; Alissa Eagle Esq.

(57) ABSTRACT

The invention provides *Brassica oleracea* plants comprising a white-stem trait and methods for producing a plant produced by crossing such plants with themselves or with another plant, such as a plant of another genotype. The invention further relates to seeds and plants produced by such crossing. The invention further relates to parts of such plants.

33 Claims, 4 Drawing Sheets

WHITE-STEM TRAIT CONTAINING PLANTS

This application claims the priority of U.S. Provisional Appl. Ser. No. 61/326,036 filed Apr. 20, 2010, the entire disclosure of which is incorporated herein by reference.

BACKGROUND OF THE INVENTION

1. Field of the Invention

The present invention relates to the field of plant breeding and, more specifically, to the development of a white-stem trait in *Brassica oleracea* plants. The present invention also provides methods for producing plants comprising such a trait.

2. Description of Related Art

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

While breeding efforts to date have provided a number of useful plant lines with beneficial traits, there remains a great need in the art for new lines with further improved traits. Such plants would benefit farmers and consumers alike by improving crop yields and/or quality.

SUMMARY OF THE INVENTION

The present invention overcomes limitations of the prior art by providing a plant comprising a white-stem trait. Such a plant may be a *Brassica oleracea* subspecies, variety or cultivar, such as broccoli, cauliflower, cabbage, collard greens, Brussels sprouts, Chinese broccoli or kale. In specific embodiments, the plant is a broccoli or cauliflower plant. In certain aspects, a plant comprising the white-stem trait may be defined as comprising a stem that is substantially white- to cream-colored. In other aspects, the plant comprising the white-stem trait may be defined as comprising a stem that is substantially more white than a stem of an isogenic plant not comprising the white-stem trait. In some aspects, the stem color may be within the range encompassed by colors 155A to 155D on the Royal Horticultural Society (RHS) color chart, including intermediate colors. In some aspects, the stem color may be about 155C on the Royal Horticultural Society (RHS) color chart. In some aspects, the stem color may be 155C on the Royal Horticultural Society (RHS) color chart.

In further aspects, a plant comprising the white-stem trait may additionally comprise a petiole and/or leaf vein in which the color thereof is defined as substantially white- to cream-colored. In other aspects, a plant comprising the white-stem trait may comprise a petiole and/or leaf vein in which the color thereof is substantially more white than a petiole and/or leaf vein of an isogenic plant not comprising the white-stem trait. In some aspects, the petiole and/or leaf vein color may be within the range encompassed by colors 155A to 155D on the Royal Horticultural Society (RHS) color chart, including intermediate colors. In some aspects, the petiole and/or leaf vein color may be about 155C on the Royal Horticultural Society (RHS) color chart. In some aspects, the petiole and/or leaf vein color may be 155C on the Royal Horticultural Society (RHS) color chart.

In other aspects, a plant comprising the white-stem trait may comprise a curd that is substantially yellow- to orange-colored. In additional aspects, a plant comprising the white-stem trait may comprise a curd that is yellow to orange, including intermediate colors. In some aspects, the curd color may be within the range encompassed by colors 13A to 22D on the Royal Horticultural Society (RHS) color chart. In some aspects, the curd color may be about 16B on the Royal Horticultural Society (RHS) color chart. In some aspects, the curd color may be 16B on the Royal Horticultural Society (RHS) color chart.

In some embodiments, a plant comprising the white-stem trait of the present invention may be a hybrid plant or an inbred plant. In a further embodiment of the present invention, there is provided a plant part of a plant of the invention. In one aspect, the plant part can be a head or curd. In other aspects, the plant part can be a leaf, a floret, an ovule, pollen or a cell. In a specific aspect, seeds of plants comprising the white-stem trait are provided.

In another aspect of the invention, a tissue culture comprising regenerable cells capable of expressing the white-stem trait is provided. The tissue culture may be capable of regenerating plants expressing all of the physiological and morphological characteristics of a plant comprising the white-stem trait. The regenerable cells in such tissue cultures may be derived, for example, from embryos, meristems, cotyledons, pollen, leaves, anthers, roots, root tips, pistils, flowers, florets, seed and stalks.

In some embodiments, the combination of phenotypic traits which is defined herein as the white-stem trait may be defined as controlled by a monogenic recessive allele.

In still further embodiments, methods of introgressing the white-stem trait into a species, subspecies, cultivar and/or variety within *Brassica oleracea* are provided. The white-stem trait can be introgressed into any subspecies, cultivar and/or variety within *Brassica oleracea*, including broccoli, cauliflower, cabbage, collard greens, Brussels sprouts, Chinese broccoli or kale. In specific embodiments, the white-stem trait may be introgressed into cauliflower, and specifically into a cauliflower variety possessing the persistent-white trait as described in U.S. Patent Application Publication No. 2008-0127362 (Boon et al.).

In additional aspects, a method of producing a plant comprising a white-stem trait in accordance with the invention is provided. In one embodiment, the method comprises crossing a plant comprising at least a first allele that confers a white-stem trait with a second plant. In some aspects, the second plant can comprise at least one desired trait. In one embodiment of the invention, the first step in "crossing" comprises planting seeds of the first and second parent plants, often in proximity so that pollination will occur for example, mediated by insect vectors. Alternatively, pollen can be transferred manually.

A second step may comprise cultivating or growing the seeds of first and second parent plants into plants that bear flowers. A third step may comprise preventing self-pollination of the plants, such as by emasculating the male portions of flowers, (i.e., treating or manipulating the flowers to produce an emasculated parent plant). Self-incompatibility systems may also be used for the same purpose. Self-incompatible plants shed viable pollen and have fertile ovules, and can pollinate or be pollinated by plants of other varieties, but are incapable of pollinating themselves or other plants of the same line. F1 progeny can be produced from a cross.

A third step in breeding a plant comprising a white-stem trait may comprise selecting an F1 progeny which comprises an allele that confers the white-stem trait. A fourth step in breeding a plant with a white-stem trait can comprise selfing the selected F1 progeny or a subsequent progeny thereof to recover a progeny plant homozygous for said allele and expressing the white-stem trait. The present invention also provides plants produced by such methods.

In additional aspects, methods are provided for introducing a desired trait into a plant in accordance with the invention. In one embodiment, a first step in introducing a desired trait comprises crossing a plant comprising at least a first allele that confers the white-stem trait, with a second plant capable of being crossed with the plant comprising the first allele. A second step may comprise selecting an F1 progeny that comprises said allele. A third step may comprise crossing the selected F1 progeny plant with itself or a further plant. In particular embodiments, backcrossing may be used to recover a plant of a desired genotype into which the white stem trait has been introgressed. A fourth step may therefore comprise selecting backcross progeny homozygous for the allele and that otherwise comprises essentially all of the traits of a recurrent parent used in the backcrossing.

One embodiment of the present invention provides a method of vegetatively propagating a plant comprising and/or expressing a white-stem trait. Vegetative propagation of a plant can comprise collecting tissue capable of being propagated from a plant comprising and/or expressing a white-stem trait. Vegetative propagation of a plant can further comprise cultivating said tissue to obtain proliferated shoots. Vegetative propagation of such a plant can additionally comprise rooting said proliferated shoots to obtain rooted plantlets. Optionally, the rooted plantlets can be grown into plants.

In another aspect of the invention, a plant comprising a white-stem trait and an added heritable trait is provided. The heritable trait may comprise a genetic locus that is, for example, a dominant or recessive allele. In certain embodiments of the invention, a plant comprising a white-stem trait is defined as comprising a single locus conversion. In specific embodiments of the invention, an added genetic locus confers one or more traits such as, for example, herbicide tolerance, insect resistance, disease resistance, male sterility and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The present invention also provides the seeds and plants produced by a process that comprises crossing a first parent plant with a second parent plant, wherein at least one of the first or second parent plants is a plant comprising a white-stem trait. In one embodiment of the invention, seed and plants produced by the process are first generation ($F_1$) hybrid seed and plants produced by crossing a plant in accordance with the invention with another, distinct plant. The present invention further contemplates plant parts of such an $F_1$ hybrid plant, and methods of use thereof. Therefore, certain exemplary embodiments of the invention provide an $F_1$ hybrid plant and seed thereof. In still yet another aspect, the present invention provides a method of producing a plant derived from a plant comprising a white-stem trait, the method comprising the steps of: (a) preparing a progeny plant derived from a plant comprising a white-stem trait, wherein said preparing comprises crossing a plant of the plant comprising a white-stem trait with a second plant; and (b) crossing the progeny plant with itself or a second plant to produce a seed of a progeny plant of a subsequent generation. In certain embodiments, the plant comprising the white-stem trait is the female parent. In other embodiments, the plant comprising the white-stem trait is the male parent.

In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from a plant comprising a white-stem trait. The plant derived from a plant comprising a white-stem trait may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from a plant comprising a white-stem trait is obtained which possesses some of the desirable traits of the line as well as potentially other selected traits.

In some embodiments, the present invention provides a method of producing a plant comprising a white-stem trait and an added desired trait. This method can comprise introducing a transgene conferring the desired trait into a plant comprising the white-stem trait. In some aspects, the invention provides a plant comprising a white-stem trait and at least one transgene.

In still yet another aspect, the invention provides a method of determining the genotype of a plant comprising a white-stem trait, said method comprising detecting in the genome of the plant at least a first polymorphism. The invention further provides a method of determining the genotype of first-generation progeny of a plant comprising a white-stem trait comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In a specific embodiment of the present invention, a plant provided herein comprising the white-stem trait is a plant of broccoli line BCH 971-4. In a specific aspect, a plant of broccoli line BCH 971-4 comprises a stem that is substantially white to cream-colored. In a further aspect, a plant of broccoli line BCH 971-4 comprises a curd that is yellow- to orange-colored.

In a still further aspect of the invention, a plant of broccoli line BCH 971-4 comprising a stem, petiole and/or leaf vein color substantially more white than a stem, petiole and/or leaf vein of broccoli variety Sibsey (RS05950001, Bellaverde™) is provided. In some embodiments, the color of the stem, petiole and/or leaf vein may be within the range encompassed by colors 155A to 155D on the Royal Horticultural Society (RHS) color chart. In further embodiments, a plant of broccoli line BCH 971-4 may comprise a stem, petiole and/or leaf vein defined as having stem and leaf vein color of about 155C according to the Royal Horticultural Society (RHS) color chart. In still further embodiments of the invention, broccoli plants are provided exhibiting a yellow- to orange-colored curd, including intermediate colors. In some embodiments, the color of the curd may be within the range encompassed by colors 13A to 22D on the Royal Horticultural Society (RHS) color chart. In specific embodiments, the color of the curd, as measured by the Royal Horticultural Society (RHS) color chart, may be defined as 16B.

In further embodiments, a plant of broccoli line BCH 971-4 may be defined as having stems which, at harvest, are substantially white on the outside and light green on the inside. The stems may remain white on the outside after cooking. In still further embodiments of the invention, the leaf petiole of a plant of the invention is white or substantially white. In some aspects, the white or substantially white petioles are present at or before the developmental stage at which the plant has a first true leaf. In further aspects, the petioles of the cotyledons are white or substantially white.

In still further embodiments, a plant of broccoli line BCH 971-4 produces leaves that are green or light green. In some aspects, the green or light green leaf color is present at or before the developmental stage at which the plant has a first true leaf. In particular aspects, the leaf veins of a plant according to the invention are white or substantially white. In additional aspects, the white leaf veins are present at or before the developmental stage at which the plant has a first true leaf. In some aspects, the white or substantially white leaf veins are present in the cotyledons.

In another aspect, the invention provides a plant of broccoli line BCH 971-4 that exhibits a combination of traits comprising stems which are white on the outside and light green on the inside at harvest; a plant in which the stems remain white on the outside after cooking; a plant which has a yellow- to orange-colored curd; and a plant with a leaf that is green or light green and has a white vein and petiole. In some embodiments, the combination of phenotypic traits may be defined as controlled by a monogenic recessive allele.

In some embodiments of the present invention, the broccoli plant which comprises the white-stem trait can be broccoli line BCH 971-4, a sample of seed of said broccoli line BCH 971-4 having been deposited under ATCC Accession Number PTA-10298. In some embodiments, the plant which comprises the white-stem trait can be a progeny of broccoli line BCH 971-4, including both broccoli and cauliflower plants, such as floretting cauliflower plants, derived from BCH 971-4.

In various aspects, a plant of broccoli line BCH 971-4 can be used as a parental line of any ancestral generation for breeding a broccoli or a cauliflower plant which comprises the white-stem trait. In some aspects, a progeny of broccoli line BCH 971-4 can be used as a broccoli or cauliflower plant for breeding a broccoli or cauliflower plant, such a floretting cauliflower plant, which comprises the white-stem trait.

Additionally, a desired trait can be introduced into broccoli line BCH 971-4 or a progeny thereof using the methods of the present invention.

In still another aspect, the invention provides a seed that produces a broccoli or cauliflower plant comprising a white-stem trait as described herein. In certain embodiments, the invention provides a cauliflower plant comprising both a white stem trait and brilliant white trait, which may further be a floretting cauliflower. In a further embodiment of the present invention, there is provided a plant part of a plant of the invention. In one aspect, the plant part can be a head of broccoli or cauliflower. In other aspects, the plant part can be a leaf, a floret, an ovule, pollen, a curd or a cell. In various aspects, the seed of broccoli line BCH 971-4, or its progeny is provided. A plant of broccoli line BCH 971-4 can be used for producing seed, and, in some embodiments, the seed produced from broccoli line BCH 971-4 may be hybrid.

In certain embodiments, the *Brassica oleracea* plant exhibiting the white stem trait is a cauliflower (*Brassica oleracea* var. *botrytis*) plant also comprising the brilliant white (BW) trait. In yet other embodiments, the cauliflower plant may further comprise a floretting trait.

Another aspect of the invention provides a method for producing seed comprising the steps of: (a) crossing a plant according to claim 1 with itself or a second plant capable of being crossed thereto; and (b) allowing seed to form, wherein the plant according to claim 1 is a plant of broccoli line BCH 971-4, a sample of seed of said broccoli line having been deposited under ATCC Accession Number PTA-10298, and further wherein the second plant is a plant of a cauliflower line comprising the brilliant white (BW) trait. In a particular embodiment of the method, the second plant is a plant of cauliflower line CLP/NY6633(02:310-2) having been deposited under NCIMB Accession Number 41430. A further aspect of the invention provides a method of producing a floretting cauliflower plant with a white stem, said method comprising: (a) crossing a broccoli plant comprising at least a first allele that confers a white stem when in a homozygous state with a cauliflower plant comprising a floretting trait and a brilliant white trait to produce F1 progeny; (b) selecting at least a first F1 progeny that comprises the allele; (c) selfing said progeny or a subsequent progeny thereof to recover a progeny cauliflower plant homozygous for said allele and comprising said white stem and floretting cauliflower phenotype.

Another aspect of the invention provides a method of producing cauliflower comprising: (a) obtaining a *Brassica oleracea* plant exhibiting the white-stem trait wherein the plant is a cauliflower plant; and (b) collecting cauliflower from the plant.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

In particular embodiments of the invention, a plant or any trait thereof may be described in terms of a color value(s) on the Royal Horticultural Society (RHS) color chart. This chart and the use thereof are well known in the art. It is further well known to those of skill in the art that other systems of color assessment are available and may be used to describe color in connection with any particular plant or trait thereof, including those described herein.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
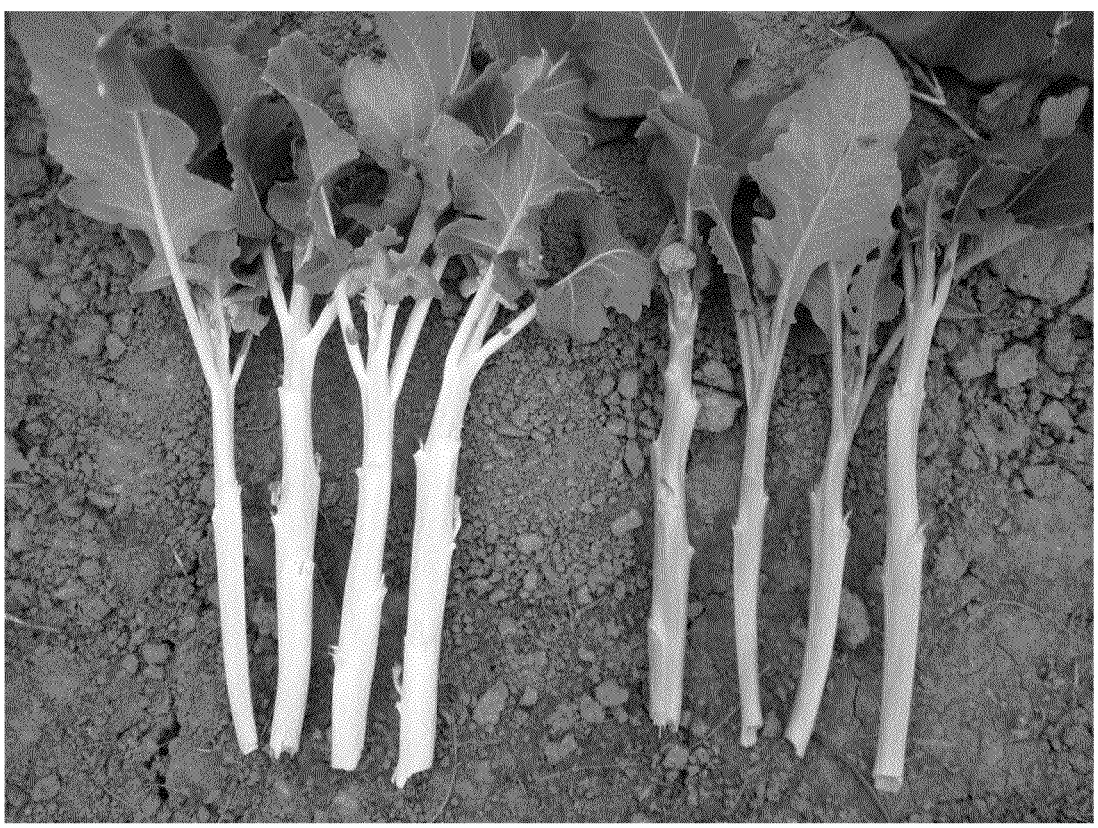
FIG. 1 is a representative photograph of the phenotype of a plant expressing the white-stem trait. Broccoli line BCH 971-4 (four stalks on left) and comparison variety Sibsey (RS05950001, Bellaverde™, four stalks on right) are shown. The photograph shows that broccoli line BCH 971-4 has white stems, and that the leaves have white petioles and green inter-vein tissues. On some of the stalks of broccoli line BCH 971-4, a yellow curd is visible. In Sibsey (RS05950001, Bellaverde™), the stem, curd, leaf and leaf veins are all green. The photograph also shows that the green tissues of the leaves of broccoli line BCH 971-4 are a lighter shade of green than the green tissues of the leaves of Sibsey.
Figure 2:
FIG. 2 is a representative photograph of a stem, leaves and young curd of a plant expressing the white-stem trait. The photograph shows that the stem, the leaf petioles, and the leaf veins are white in broccoli line BCH 971-4. The photograph also shows that the inter-vein tissues of the leaves of broccoli line BCH 971-4 are green. The photograph further shows that the young curd of the broccoli line BCH 971-4 is a yellow-orange color.
Figure 3:
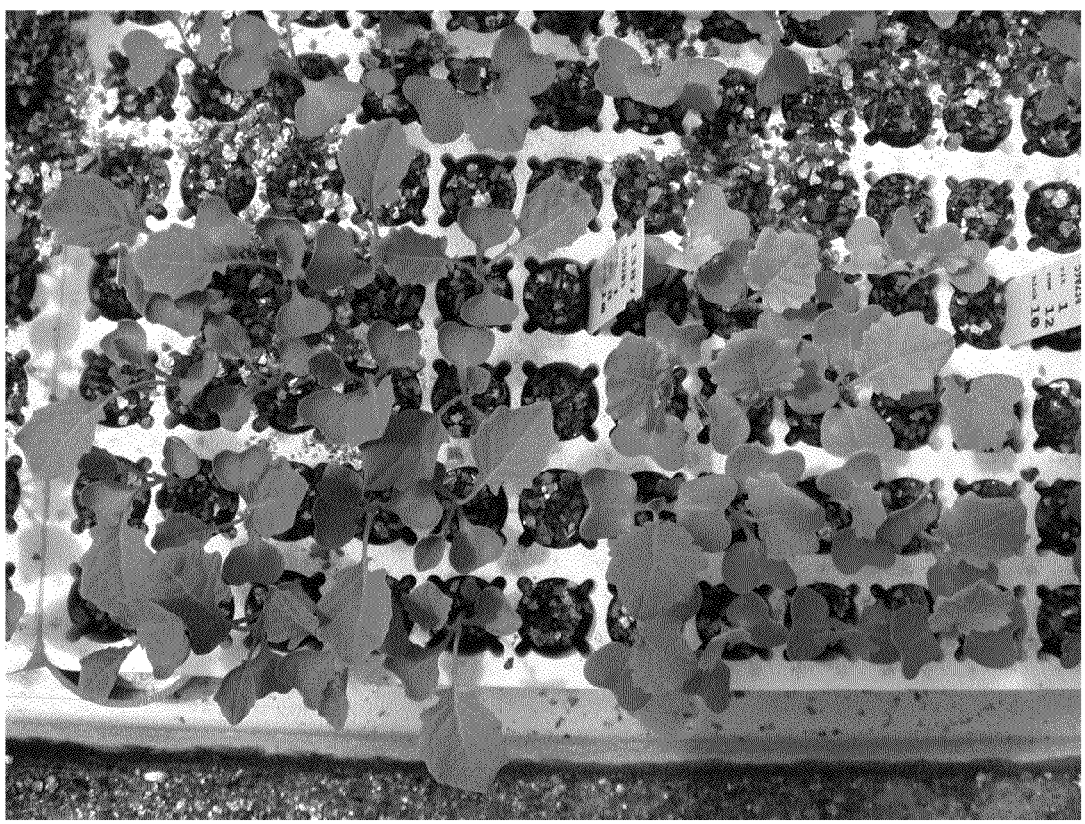
FIG. 3 is a photograph of young broccoli plants expressing the white-stem trait. The photograph shows broccoli line BCH 971-4 (four rows of seedlings to the right of the row of empty cells) and an inbred broccoli line isogenic to BCH 971-4 except that it does not comprise the white-stem trait (four rows of seedlings to the left of the empty row of cells). The photograph shows that the seedlings of line BCH 971-4 are a yellower shade of green than those of the isogenic line.

The invention provides subspecies, cultivars and varieties of *Brassica oleracea* with a white-stem trait. The white-stem trait described herein is controlled by a monogenic recessive allele.

A. Breeding Plants Comprising a White-Stem Trait

One aspect of the current invention concerns methods for producing a plant with a white-stem trait. Such methods can be used for propagation of a plant comprising a white-stem trait, or can be used to produce plants that are derived from such a plant. Plants derived from a plant with a white-stem trait may be used, in certain embodiments, for the development of new varieties of broccoli, cauliflower, cabbage, collard greens, Brussels sprouts, Chinese broccoli or kale, or any other subspecies, cultivar or variety of *Brassica oleracea*.

The development of new varieties using one or more starting varieties is well known in the art. In accordance with the invention, novel varieties may be created by crossing a plant with the white-stem trait followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true-breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give true-breeding progeny for the trait being transferred.

The plants of the present invention are particularly well suited for the development of new lines based on the elite nature of the genetic background of the plants. In selecting a second plant to cross with a plant comprising the white-stem trait, it will typically be preferred to choose those plants which either themselves exhibit one or more selected desirable characteristics or which exhibit the desired characteristic(s) when in hybrid combination. Examples of desirable traits may include, in specific embodiments, high head weight, floret size, shape and uniformity, small bead size, high domed heads, compact heads, smooth heads, large heads, early maturity, high seed yield, high seed germination, seedling vigor, high yield, disease tolerance or resistance, and adaptability for soil and climate conditions. Consumer-driven traits, such as nutritional value and taste are other traits that may be incorporated into new plants developed by this invention.

B. Further Embodiments of the Invention

The present invention provides plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those plants which are developed by a plant breeding technique called backcrossing, wherein essentially all of the desired morphological and physiological characteristics of a variety are recovered in addition to the single locus transferred into the variety via the backcrossing technique. By essentially all of the desired morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety, for example to introduce a characteristic into a plant with the white-stem trait. Backcrossing methods can also be used to introgress the white-stem trait into a different subspecies, cultivar or variety of Brassica oleracea. The parental plant which contributes the locus for the desired characteristic is termed the nonrecurrent or donor parent. This terminology refers to the fact that the nonrecurrent parent is used one time in the backcross protocol and therefore does not recur. The parental plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

Modified backcrossing may also be used with plants comprising the white-stem trait. This technique uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of broccoli plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

C. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, Agrobacterium-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant comprising the white-stem trait according to the invention. Non-limiting examples of particular genes and corresponding phenotypes one may choose to introduce into a plant comprising the white-stem trait include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

D. Origin and Breeding History of a Broccoli Plant with the White-Stem Trait Broccoli plants with a white stem and yellow- to orange-colored curd were surprisingly discovered during cultivation of a proprietary broccoli line designated 570462. Three plants with white stems and yellow-to-orange curds were selected from the progeny of 570462. Two plants from each of two of these lines (580700 and 580702) were propagated in vitro and transplanted into pots in a cage (for a total of 6 plants transplanted per clone). These twenty-four total plants were allowed to pollenate freely with one another via natural insect vectors. In bulk progeny analysis of 48 offspring from the four plants, 14 plants had white stems and yellow- to orange-colored curds and 34 plants had normal phenotypes, indicating a monogenic recessive pattern of inheritance. The progeny development can be summarized as follows:

Line 541555 F1 2(PPMN)/2(PLH42)NJA/MRA/MA×2 (PLH42)MA2/PPMN

Line 550298 F2 DEHELEGENEPOOL—4.

Line 560383 F3 DEHELEGENEPOOL—4.2.

Line 570462 F4 DEHELEGENEPOOL—4.2.2.

Line 580700 F5 DEHELEGENEPOOL—4.2.2.1.

Line 580702 F5 DEHELEGENEPOOL—4.2.2.3.

E. Physiological and Morphological Characteristics of a Broccoli Plant Comprising the White-Stem Trait In accordance with one aspect of the present invention, there is provided a broccoli plant having the white-stem trait. One example of such a plant is broccoli line BCH 971-4, which has white stems and a yellow- to orange-colored curd. A description of the physiological and morphological characteristics of this line is presented in Table 1.

TABLE 1

Physiological and Morphological Characteristics of Broccoli Line BCH 971-4

| CHARACTERISTIC | BCH 971-4 | Comparison Variety Legacy |
|---|---|---|
| Region of Adaptation Maturity, Spring Planted | NW Europe | |
| Days from transplanting to 50% harvest | 44 | 70 |
| Transplanting date | Jul. 15, 2009 | Jul. 15, 2009 |
| First harvest date | Sep. 2, 2009 | Sep. 23, 2009 |
| Last harvest date | Sep. 2, 2009 | Sep. 30, 2009 |
| Length of harvest period in days | 1 | 7 |
| Harvest season (main crop at 50% harvest) | Spring/summer, Summer, Summer/fall | Fall |
| Time of harvest maturity (50% of plants) | Very early (Earlyman, Primor) | Medium late |
| Time of beginning of flowering (50% of plants with at least 10% flowers) | Early (Clipper, Southern Comet) | Medium-late |
| Seedling | | |
| Cotyledon color | Light green | Dark green |
| RHS Color Chart value for seedling cotyledon color | 144B | 137B |
| Cotyledon anthocyanin | Weak | Weak |
| Hypocotyl anthocyanin | Weak | Strong |
| Plant | | |
| Plant height in centimeters from soil line to top of leaves | 55.0 cm | 70.0 cm |
| Head height in centimeters from soil line to top of leaves | 48.0 cm | 43.0 cm |
| Height at harvest maturity | Medium (Coaster) | Medium |
| Number of stems | More than one (A Getti di Napeli) | One |
| Branches | Many | Few |
| Habit | Spreading | Spreading |
| Market class | Fresh market | Fresh market |
| Life cycle | Annual | Annual |
| Type of variety | Inbred | Hybrid |

TABLE 1-continued

Physiological and Morphological Characteristics of Broccoli Line BCH 971-4

| CHARACTERISTIC | BCH 971-4 | Comparison Variety Legacy |
|---|---|---|
| Leaves | | |
| Outer Leaves: number of leaves per plant (at harvest) | 12 | 24 |
| Outer Leaves: width (at midpoint of plant including petiole) | 25.0 cm | 25.0 cm |
| Leaf: width | Medium (Buccaneer, Green Belt) | Medium |
| Outer Leaves: length (at midpoint of plant including petiole) | 45.0 cm | 61.0 cm |
| Leaf: length (including petiole) | Medium (Brigadeer, Sumosun) | Long |
| Outer Leaves: petiole length | 18.0 cm | 20.0 cm |
| Petiole: length | Medium (Emperor, Ramoso Calabrese) | Medium |
| Outer Leaves: leaf ratio-length/width | 2:1 | 3:1 |
| Outer Leaves: leaf attachment | Petiolate | Petiolate |
| Outer Leaves: wax presence | Weak | Intermediate |
| Leaf: number of lobes | Few (Early White Sprouting) | Few |
| Outer Leaves: foliage color (with wax, if present) | Light green | Medium |
| Outer Leaves: foliage color (with wax, if present; RHS color chart value) | 139C | 136B |
| Leaf blade: color | Green (Claudia, Verflor)/ Light green | Grey green |
| Leaf blade: intensity of color | Light | Medium |
| Leaf blade: anthocyanin coloration | Absent (Claudia, Embassy) | Absent |
| Leaf blade: undulation of margin | Weak (Beufort, Early Pack, Laser, Paladin) | Medium |
| Leaf blade: dentation of margin | Weak (Galaxy) | Weak |
| Outer Leaves: leaf shape | Elliptic | Elliptic |
| Outer Leaves: leaf base | Blunt | Blunt |
| Outer Leaves: leaf apex | Blunt | Blunt |
| Outer Leaves: leaf margins | Slightly wavy | Very wavy |
| Outer Leaves: leaf veins | Thin | Intermediate |
| Outer Leaves: midrib | Slightly raised | Slightly raised |
| Leaf blade: blistering | Absent or very weak (Buccaneer, Colbert) | Weak |
| Outer Leaves: attitude (leaf angle from ground) | Horizontal (0-15 degrees) | Semi-erect |
| Leaf: attitude (at beginning of head formation) | Semi-erect (Arcadia, Asti, Civet, Claudia) | Semi-erect |
| Outer Leaves: torsion of leaf tip | Weak | None |
| Outer Leaves: profile of upper side of leaf | Planar | Planar |
| Head | | |
| Length of branching at base (excluding stem) | Short (Brigadeer, Buccaneer Emperor) | Short |
| Diameter at widest point (at market maturity) | 11.0 cm | 16.0 cm |
| Depth (at market maturity) | 8.0 cm | 8.0 cm |
| Weight, market trimmed (at market maturity) | 90.0 gm | 400.0 gm |
| Color | Yellow/orange | Grey-green |
| Intensity of color | Light | Medium |
| RHS Color Chart value for head color | 16B | N138C |
| Anthocyanin coloration | Absent (Early White Sprouting) | Present |
| Intensity of anthocyanin coloration | N/A | Very weak |
| Shape (at market maturity) | Transverse elliptic (Buccaneer, Futura) | Transverse broad elliptic |
| Dome shape (at market maturity) | Semi-domed | Domed |
| Size (at market maturity) | Very small (Early Purple Sprouting) | Large |
| Compactness/firmness (at market maturity) | Medium (Late Corona) | Firm |

TABLE 1-continued

Physiological and Morphological Characteristics of Broccoli Line BCH 971-4

| CHARACTERISTIC | BCH 971-4 | Comparison Variety Legacy |
|---|---|---|
| Surface knobbling (at market maturity) | Coarse (Perseus, Regillo) | Medium |
| Texture | Medium (Clipper, Coaster) | Fine |
| Bead size (at market maturity) | Small | Small |
| Flower buds (at market maturity) | Even in size | Even |
| Anthocyanin coloration of leaf axils (at market maturity) | Absent | Absent |
| Anthocyanin coloration of leaf veins (at market maturity) | Absent | Absent |
| Anthocyanin coloration of leaf blade (at market maturity) | Absent | Absent |
| Head: Anthocyanin coloration of entire plant (at market maturity) | Absent | Absent |
| Anthocyanin coloration of leaf petiole (at market maturity) | Absent (Claudia, Embassy) | Absent |
| Color of head leaves (at market maturity) | No head leaves present | Green |
| RHS Color Chart value for the color of head leaves | N/A | 136B |
| Bracts | Absent (Gem, Orion) | Present |
| Secondary heads (at market maturity) | Combination | Absent |
| Prominence of secondary heads (at market maturity) | Strong (Marathon, Tribute) | Weak |
| Number of secondary heads (at market maturity) | 6 | 0 |
| Flower | | |
| Color | Cream | Yellow |
| Intensity of yellow color | Light (Brigadeer) | Medium |
| Color | 5D | 5B |
| Stalk color | Green | Green |
| RHS Color Chart value for flower stalk color | 145D | 138B |
| Male sterility | Absent (Marathon) | Absent |

*These are typical values. Values may vary due to environment. Other values that are substantially equivalent are also within the scope of the invention.

Figure 4:
FIG. 4 is a photograph of a young cauliflower plant expressing the white-stem trait. On the left is an F2 cauliflower plant derived from a cross of BCH971-4 with a cauliflower line exhibiting the brilliant white trait; followed by selection for cauliflower phenotype On the right is a normal cauliflower.

F. Origin and Breeding History of a Cauliflower Plant with the White-Stem Trait Broccoli plant BCH971-4 was crossed to Brilliant White cauliflower line CLP/NY6633 (02:310-2; seed of which has been deposited at NCIMB under Accession No. 41430, and in the F2 generation a plant was selected with white stem and cauliflower phenotype (i.e. inflorescence meristems developing in place of floral meristems), a young plant of which is shown in FIG. 4. On the left is a representative F2 cauliflower plant with white stem; on the right is a normal cauliflower plant. F2 seed was prepared.

Plants grown from such F2 seed may be utilized for breeding a brilliant white floretting cauliflower with a white stem. For instance, this cauliflower may be crossed with a brilliant white floretting cauliflower, to obtain a brilliant white floretting white stem cauliflower.

G. Physiological and Morphological Characteristics of a Cauliflower Plant Comprising the White-Stem Trait In accordance with one aspect of the present invention, there is provided a cauliflower plant having the white-stem trait. One example of such a plant is the white stem cauliflower plant shown in FIG. 4, which is a progeny plant of broccoli BCH971-4 crossed with cauliflower CLP/NY6633 (02:310:2). Progeny plants may be selected which comprise brilliant white, white stem, and floretting traits.

H. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a broccoli variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a broccoli plant by transformation.

G. Deposit Information

A deposit of broccoli line BCH 971-4, disclosed above and recited in the claims, has been made with the American Type Culture Collection (ATCC), 10801 University Blvd., Manassas, Va. 20110-2209. The date of the deposit was Aug. 21, 2009. The accession number for those deposited seeds of broccoli line BCH 971-4 is ATCC Accession Number PTA-10298. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

A deposit of cauliflower line CLP/NY6633(02:310-2), disclosed above and recited in the claims has been made with NCIMB Ltd., Ferguson Bldg., Craibstone Estate, Bucksburn, Aberdeen A B21 9YA, Scotland. The accession number for those deposited seeds of cauliflower line CLP/NY6633(02: 310-2) is #41430. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A broccoli (*Brassica oleracea* var. *italica*) or cauliflower (*Brassica oleracea* var. *botrytis*) plant exhibiting a white stem trait characterized by a stem color in the range of colors 155A to 155D on the Royal Horticultural Society (RHS) color chart, wherein said white-stem trait is conferred by a monogenic recessive allele found in the genome of broccoli line BCH 971-4, and wherein a sample of seed of said broccoli line BCH 971-4 has been deposited under ATCC Accession Number PTA-10298.

2. The plant of claim 1, wherein the plant is hybrid.

3. The plant of claim 1, wherein the plant is inbred.

4. The plant of claim 1, further comprising an allele conferring male sterility.

5. The plant of claim 1, wherein the plant comprises a transgene.

6. A plant part of the plant of claim 1.

7. The plant part of claim 6, further defined as a leaf, a floret, an ovule, pollen, a cell, a curd or a head.

8. A seed that produces the plant of claim 1.

9. A tissue culture of regenerable cells of the plant of claim 1.

10. The tissue culture according to claim 9, comprising cells or protoplasts from a plant part selected from the group consisting of embryos, meristems, cotyledons, pollen, leaves, anthers, roots, root tips, pistil, flower, florets, curds, seed and stalks.

11. A plant regenerated from the tissue culture of claim 10, wherein the regenerated plant comprises the white-stem trait.

12. A method of vegetatively propagating the plant of claim 1 comprising the steps of:
    (a) collecting tissue capable of being propagated from a plant of claim 1;
    (b) cultivating said tissue to obtain proliferated shoots; and
    (c) rooting said proliferated shoots to obtain rooted plantlets.

13. The method of claim 12, further comprising growing plants from said rooted plantlets.

14. A method of introducing a desired trait into the plant of claim 1 comprising:
    (a) crossing the plant according to claim 1 with a second plant that comprises a desired trait to produce F1 progeny;
    (b) selecting an F1 progeny that comprises the desired trait;
    (c) crossing the selected F1 progeny with a plant according to claim 1 to produce backcross progeny; and
    (d) repeating steps (c) and (d) three or more times in succession to produce selected fourth or higher backcross progeny that comprise the desired trait.

15. A plant produced by the method of claim 14, wherein the plant comprises the desired trait and at least a first allele that confers a white stem trait.

16. A method of producing a plant comprising an added desired trait, the method comprising introducing a transgene conferring the desired trait into the plant according to claim 1.

17. A method for producing seed comprising the steps of:
    (a) crossing the first plant according to claim 1 with itself or a second plant capable of being crossed thereto; and
    (b) allowing seed to form.

18. The method of claim 17, further comprising the steps of:
    (c) crossing a plant grown from said seed of step (b) with itself or a second plant at least one additional time to yield additional seed.

19. The method of claim 17, wherein the first plant is a plant of broccoli line BCH 971-4, a sample of seed of said broccoli line having been deposited under ATCC Accession Number PTA-10298.

20. A method of producing a broccoli plant with a white stem and yellow- to orange-colored curd, said method comprising:
    (a) crossing a broccoli plant comprising at least a first allele that confers a white stem and yellow- to orange-colored curd when in a homozygous state with a second broccoli plant to produce F1 progeny;
    (b) selecting at least a first F1 progeny that comprises the allele; and
    (c) selfing said progeny or a subsequent progeny thereof to recover a progeny broccoli plant homozygous for said allele and comprising said white stem and yellow- to orange-colored curd;
wherein said white stem falls within the range encompassed by colors 155A to 155D and said yellow-to orange-colored curd trait falls within the range encompassed by colors 13A to 22D on the Royal Horticultural Society (RHS) color chart, wherein said allele is found in the genome of broccoli line BCH 971-4, and wherein a sample of seed of said broccoli line BCH 971-4 has been deposited under ATCC Accession Number PTA-10298.

21. The method of claim 20, wherein said first allele has been inherited from broccoli line BCH 971-4 or a progeny of any generation thereof comprising said allele from broccoli line BCH 971-4, a sample of seed of said broccoli line BCH 971-4 having been deposited under ATCC Accession Number PTA-10298.

22. The method of claim 17, wherein the second plant is of an inbred broccoli line.

23. An F1 hybrid seed having a plant of broccoli line BCH 971-4 as one parent, wherein a sample of seed of said broccoli line has been deposited under ATCC Accession Number PTA-10298.

24. The F1 hybrid seed of claim 23, wherein the plant of line BCH 971-4 is a male parent.

25. The F1 hybrid seed of claim 23, wherein the plant of line BCH 971-4 is a female parent.

26. A plant produced by growing the seed of claim 23.

27. A plant part of the plant of claim 26.

28. The plant part of claim 27, further defined as a leaf, a floret, an ovule, pollen, a cell, a curd or a head of broccoli.

29. A method of producing broccoli comprising:
    (a) obtaining the plant of claim 1; and
    (b) collecting broccoli from the plant.

30. The seed of claim 8, further defined as a seed of broccoli line BCH 971-4, a sample of seed of said broccoli line BCH 971-4 having been deposited under ATCC Accession Number PTA-10298.

31. The method of claim 17, wherein the first plant is a plant of broccoli line BCH 971-4, a sample of seed of said broccoli line having been deposited under ATCC Accession Number PTA-10298, and further wherein the second plant is a plant of a cauliflower line comprising a brilliant white (BW) trait, wherein seed comprising said brilliant white trait have been deposited under NCIMB Accession Number 41430.

32. A method of producing cauliflower comprising:
    (a) obtaining the plant of claim 1; and
    (b) collecting cauliflower from the plant.

33. The plant of claim 1, wherein said white-stem trait is introgressed into the plant from broccoli line BCH 971-4 or a progeny thereof that inherited said white-stem trait from broccoli line BCH 971-4, a sample of seed of said broccoli line having been deposited under ATCC Accession Number PTA-10298.

* * * * *